(12) United States Patent
Wang et al.

(10) Patent No.: US 8,322,046 B2
(45) Date of Patent: *Dec. 4, 2012

(54) POWDER FORMATION BY ATMOSPHERIC SPRAY-FREEZE DRYING

(76) Inventors: Zhaolin Wang, Edmonton (CA);
Warren H. Finlay, Edmonton (CA)

( * ) Notice: Subject to any disclaimer, the term of this patent is extended or adjusted under 35 U.S.C. 154(b) by 531 days.

This patent is subject to a terminal disclaimer.

(21) Appl. No.: 12/050,654

(22) Filed: Mar. 18, 2008

(65) Prior Publication Data
US 2008/0155853 A1    Jul. 3, 2008

Related U.S. Application Data

(63) Continuation of application No. 11/318,864, filed on Dec. 28, 2005, now Pat. No. 7,363,726, which is a continuation of application No. 10/762,300, filed on Jan. 23, 2004, now Pat. No. 7,007,406.

(30) Foreign Application Priority Data

Dec. 22, 2003 (CA) .................................... 2450779

(51) Int. Cl.
*F26B 21/06* (2006.01)
(52) U.S. Cl. .......... 34/286; 34/287; 34/288; 34/289; 34/295; 34/296; 424/46; 424/497; 134/172; 436/174; 514/2; 514/573; 510/295; 510/418
(58) Field of Classification Search ............ 34/286, 34/287, 288, 289, 295, 296, 92, 285; 424/46, 424/497; 134/172; 436/174; 514/573, 2; 510/295, 418
See application file for complete search history.

(56) References Cited

U.S. PATENT DOCUMENTS

| | | | | |
|---|---|---|---|---|
| 2,460,546 A | * | 2/1949 | Stephanoff | 523/319 |
| 2,856,278 A | * | 10/1958 | Bray et al. | 71/25 |
| 3,172,546 A | * | 3/1965 | Schreiner | 241/23 |
| 3,247,014 A | * | 4/1966 | Goldberger et al. | 427/450 |
| 3,252,776 A | * | 5/1966 | Strickland et al. | 65/469 |
| 3,257,815 A | * | 6/1966 | Brocoff et al. | 62/57 |
| 3,309,777 A | * | 3/1967 | Hutton | 34/287 |
| 3,313,032 A | | 4/1967 | Malecki | |
| 3,319,344 A | * | 5/1967 | Sachsel et al. | 34/287 |

(Continued)

FOREIGN PATENT DOCUMENTS

AU    2004269422 A1    3/2005
(Continued)

OTHER PUBLICATIONS

H. Leuenberger, "Spray freeze-drying= the process of choice for low water soluble drugs?", Journal of Nanoparticle Research, 2002, 4: 111-119.

(Continued)

*Primary Examiner* — Stephen M. Gravini
(74) *Attorney, Agent, or Firm* — Anthony R. Lambert (57) ABSTRACT

A method of manufacturing heat-sensitive pharmaceutical powder is disclosed. The original pharmaceutical substances are dissolved in a solution or suspended in a suspension, which is sprayed through an atomizing nozzle and frozen in a cold gas phase or liquid nitrogen atomized directly in the spray-freeze chamber or gas jacket at the same time (for cooling purposes). The particles are freeze-dried at roughly atmospheric pressure in a down-stream fluid flow with exit filter thereby to remove moisture entrapped on or inside the frozen particles. The system has applicability for forming other powders.

15 Claims, 3 Drawing Sheets

U.S. PATENT DOCUMENTS

| | | | |
|---|---|---|---|
| 3,490,355 A * | 1/1970 | Groth et al. | 426/473 |
| 3,565,039 A * | 2/1971 | Remer | 118/643 |
| 3,677,405 A * | 7/1972 | Keith, Jr. | 210/774 |
| 3,749,378 A * | 7/1973 | Rhodes | 261/78.2 |
| 3,788,095 A * | 1/1974 | Murphy et al. | 62/347 |
| 3,793,003 A * | 2/1974 | Othmer | 75/674 |
| 3,819,336 A * | 6/1974 | Rogers et al. | 23/302 A |
| 3,848,068 A * | 11/1974 | Rice | 423/335 |
| 3,853,541 A * | 12/1974 | Othmer | 75/677 |
| 3,938,988 A * | 2/1976 | Othmer | 75/10.21 |
| 4,015,749 A * | 4/1977 | Arzberger et al. | 222/640 |
| 4,033,048 A * | 7/1977 | Van Ike | 34/92 |
| 4,094,808 A * | 6/1978 | Stewart et al. | 252/186.26 |
| 4,161,084 A * | 7/1979 | Arny et al. | 47/2 |
| 4,273,790 A * | 6/1981 | Bosco et al. | 426/335 |
| 4,273,795 A * | 6/1981 | Bosco et al. | 426/602 |
| 4,276,381 A * | 6/1981 | Sakimae et al. | 435/179 |
| 4,324,707 A * | 4/1982 | Hungerford | 524/173 |
| 4,389,794 A * | 6/1983 | Bitterly | 34/287 |
| 4,393,817 A * | 7/1983 | Lindberg | 123/3 |
| 4,409,253 A * | 10/1983 | Morrison et al. | 426/424 |
| 4,409,931 A * | 10/1983 | Lindberg | 123/25 R |
| 4,455,135 A * | 6/1984 | Bitterly | 432/1 |
| 4,533,572 A * | 8/1985 | Neelameggham et al. | 427/216 |
| 4,541,367 A * | 9/1985 | Lindberg | 123/25 M |
| 4,541,867 A * | 9/1985 | Neelameggham et al. | 75/328 |
| 4,608,764 A | 9/1986 | Leuenberger | |
| 4,652,434 A * | 3/1987 | Bonsack et al. | 423/155 |
| 4,768,446 A * | 9/1988 | Wilkes et al. | 110/262 |
| 4,775,000 A * | 10/1988 | Ayers | 164/464 |
| 4,802,286 A * | 2/1989 | Kobayashi et al. | 34/92 |
| 4,820,627 A * | 4/1989 | McGeehan | 435/4 |
| 4,836,982 A * | 6/1989 | Brupbacher et al. | 420/129 |
| 4,837,005 A * | 6/1989 | Brode et al. | 424/47 |
| 4,851,722 A * | 7/1989 | Zauderer | 310/11 |
| 4,873,293 A * | 10/1989 | Brode et al. | 525/417 |
| 4,915,905 A * | 4/1990 | Kampe et al. | 420/418 |
| 5,009,994 A * | 4/1991 | McGeehan | 435/4 |
| 5,015,534 A * | 5/1991 | Kampe et al. | 428/570 |
| 5,019,311 A * | 5/1991 | Koslow | 264/121 |
| 5,090,132 A * | 2/1992 | Kobayashi et al. | 34/302 |
| 5,124,162 A * | 6/1992 | Boskovic et al. | 426/96 |
| 5,147,722 A * | 9/1992 | Koslow | 428/402 |
| 5,208,998 A * | 5/1993 | Oyler, Jr. | 34/288 |
| 5,230,162 A * | 7/1993 | Oyler, Jr. | 34/292 |
| 5,230,915 A * | 7/1993 | Shahidi et al. | 426/240 |
| 5,240,656 A * | 8/1993 | Scheeres | 264/297.1 |
| 5,269,077 A * | 12/1993 | Bruttini | 34/92 |
| 5,348,566 A * | 9/1994 | Sawyer et al. | 75/10.24 |
| 5,387,489 A * | 2/1995 | Fuller et al. | 430/115 |
| 5,402,992 A * | 4/1995 | Saxena | 266/202 |
| 5,426,003 A * | 6/1995 | Spengler et al. | 429/27 |
| 5,455,057 A * | 10/1995 | Symbolik et al. | 426/385 |
| 5,468,427 A * | 11/1995 | Stangle et al. | 264/3.4 |
| 5,518,709 A * | 5/1996 | Sutton et al. | 424/9.52 |
| 5,523,065 A * | 6/1996 | Stangle et al. | 423/71 |
| 5,531,845 A * | 7/1996 | Flanigan et al. | 149/109.6 |
| 5,536,893 A * | 7/1996 | Gudmundsson | 585/15 |
| 5,611,973 A * | 3/1997 | Gurfein et al. | 424/5 |
| 5,612,053 A * | 3/1997 | Baichwal et al. | 424/440 |
| 5,641,349 A * | 6/1997 | Koubek et al. | 106/206.1 |
| 5,651,952 A * | 7/1997 | Grudnoff et al. | 423/621 |
| 5,651,966 A * | 7/1997 | Read et al. | 424/93.72 |
| 5,656,498 A * | 8/1997 | Iijima et al. | 436/10 |
| 5,660,774 A * | 8/1997 | Stangle et al. | 505/425 |
| 5,665,276 A * | 9/1997 | Kirby et al. | 264/3.1 |
| 5,674,468 A * | 10/1997 | Klaveness et al. | 424/9.3 |
| 5,676,925 A * | 10/1997 | Klaveness et al. | 424/9.3 |
| 5,727,333 A * | 3/1998 | Folan | 34/285 |
| 5,731,540 A * | 3/1998 | Flanigan et al. | 149/109.6 |
| 5,738,865 A * | 4/1998 | Baichwal et al. | 424/440 |
| 5,772,912 A * | 6/1998 | Lockyer et al. | 252/70 |
| 5,780,055 A * | 7/1998 | Habib et al. | 424/464 |
| 5,785,976 A * | 7/1998 | Westesen et al. | 424/400 |
| 5,795,562 A * | 8/1998 | Klaveness et al. | 424/9.52 |
| 5,829,255 A * | 11/1998 | Sitnyakovsky et al. | 60/688 |
| 5,837,193 A * | 11/1998 | Childers et al. | 422/28 |
| 5,843,347 A * | 12/1998 | Nguyen et al. | 264/9 |
| 5,885,486 A * | 3/1999 | Westesen et al. | 428/402.24 |
| 5,902,608 A * | 5/1999 | Read et al. | 424/532 |
| 5,928,469 A * | 7/1999 | Franks et al. | 159/48.1 |
| 5,957,848 A * | 9/1999 | Sutton et al. | 600/458 |
| 5,993,804 A * | 11/1999 | Read et al. | 424/93.72 |
| 6,015,546 A * | 1/2000 | Sutton et al. | 424/9.52 |
| 6,022,525 A * | 2/2000 | Sutton et al. | 424/9.52 |
| 6,050,990 A * | 4/2000 | Tankovich et al. | 606/9 |
| 6,074,737 A * | 6/2000 | Jordan et al. | 428/312.8 |
| 6,187,226 B1 * | 2/2001 | Detering et al. | 252/373 |
| 6,207,178 B1 * | 3/2001 | Westesen et al. | 424/405 |
| 6,248,363 B1 * | 6/2001 | Patel et al. | 424/497 |
| 6,251,193 B1 * | 6/2001 | Rossy et al. | 127/2 |
| 6,251,463 B1 * | 6/2001 | Rossy et al. | 426/533 |
| 6,261,679 B1 * | 7/2001 | Chen et al. | 428/317.9 |
| 6,284,282 B1 * | 9/2001 | Maa et al. | 424/499 |
| 6,287,550 B1 * | 9/2001 | Trinh et al. | 424/76.6 |
| 6,344,182 B1 * | 2/2002 | Sutton et al. | 424/9.52 |
| 6,348,186 B1 * | 2/2002 | Sutton et al. | 424/9.52 |
| 6,372,258 B1 * | 4/2002 | Platz et al. | 424/489 |
| 6,387,394 B1 * | 5/2002 | Baichwal et al. | 424/440 |
| 6,391,224 B1 * | 5/2002 | Wowk | 252/70 |
| 6,395,197 B1 * | 5/2002 | Detering et al. | 252/373 |
| 6,413,458 B1 * | 7/2002 | Pearce | 264/141 |
| 6,416,741 B1 * | 7/2002 | Sutton et al. | 424/9.52 |
| 6,426,210 B1 * | 7/2002 | Franks et al. | 435/260 |
| 6,440,336 B1 | 8/2002 | Weinreich et al. | |
| 6,440,463 B1 * | 8/2002 | Feldstein et al. | 424/489 |
| 6,460,376 B1 * | 10/2002 | Jeanvoine et al. | 65/134.2 |
| 6,470,592 B2 * | 10/2002 | Akimoto et al. | 34/92 |
| 6,471,993 B1 * | 10/2002 | Shastri et al. | 424/486 |
| 6,509,006 B1 * | 1/2003 | Platz et al. | 424/46 |
| 6,541,001 B1 * | 4/2003 | Gallili et al. | 424/184.1 |
| 6,565,927 B1 * | 5/2003 | Drzal et al. | 427/487 |
| 6,569,405 B1 * | 5/2003 | Sutton et al. | 424/9.52 |
| 6,569,463 B2 * | 5/2003 | Patel et al. | 424/497 |
| 6,572,910 B2 * | 6/2003 | Lanner et al. | 426/438 |
| 6,582,728 B1 * | 6/2003 | Platz et al. | 424/489 |
| 6,592,869 B2 * | 7/2003 | Gallili et al. | 424/184.1 |
| 6,603,054 B2 * | 8/2003 | Chen et al. | 604/369 |
| 6,616,858 B2 * | 9/2003 | Fahy et al. | 252/70 |
| 6,630,121 B1 | 10/2003 | Sievers et al. | |
| 6,673,335 B1 * | 1/2004 | Platz et al. | 424/45 |
| 6,695,238 B2 * | 2/2004 | Inoki et al. | 241/39 |
| 6,716,629 B2 * | 4/2004 | Hess et al. | 435/420 |
| 6,739,152 B2 * | 5/2004 | Jeanvoine et al. | 65/346 |
| 6,749,554 B1 * | 6/2004 | Snow et al. | 600/3 |
| 6,797,258 B2 * | 9/2004 | Platz et al. | 424/45 |
| 6,825,031 B2 * | 11/2004 | Franks et al. | 435/260 |
| 6,830,767 B2 * | 12/2004 | Teras et al. | 426/439 |
| 6,862,890 B2 | 3/2005 | Williams et al. | |
| 6,893,645 B1 * | 5/2005 | Loughman | 424/400 |
| 6,921,527 B2 * | 7/2005 | Platz et al. | 424/45 |
| 6,923,988 B2 * | 8/2005 | Patel et al. | 424/489 |
| 6,931,888 B2 * | 8/2005 | Shekunov et al. | 62/540 |
| 6,936,279 B2 * | 8/2005 | Guerra-Santos et al. | 424/489 |
| 6,939,530 B2 * | 9/2005 | Sutton et al. | 424/9.52 |
| 6,941,676 B2 * | 9/2005 | Akimoto et al. | 34/176 |
| 6,973,931 B1 * | 12/2005 | King | 132/212 |
| 7,007,406 B2 * | 3/2006 | Wang et al. | 34/286 |
| 7,022,313 B2 * | 4/2006 | O'Connor et al. | 424/48 |
| 7,028,478 B2 * | 4/2006 | Prentice, III | 60/645 |
| 7,056,877 B2 * | 6/2006 | Caswell et al. | 510/439 |
| 7,060,213 B2 * | 6/2006 | Pearce | 264/176.1 |
| 7,073,349 B2 * | 7/2006 | Shekunov et al. | 62/534 |
| 7,076,822 B2 * | 7/2006 | Pearce | 5/655.5 |
| 7,089,681 B2 * | 8/2006 | Herbert et al. | 34/92 |
| 7,091,171 B2 * | 8/2006 | Caswell et al. | 510/439 |
| 7,094,451 B2 * | 8/2006 | Drzal et al. | 427/581 |
| 7,097,675 B2 * | 8/2006 | Detering et al. | 48/127.9 |
| 7,097,827 B2 * | 8/2006 | Platz et al. | 424/45 |
| 7,109,166 B1 * | 9/2006 | Moreau | 514/11 |
| 7,122,176 B2 * | 10/2006 | Stamets | 424/84 |
| 7,166,565 B2 * | 1/2007 | Caswell et al. | 510/438 |
| 7,172,766 B2 * | 2/2007 | Baichwal et al. | 424/434 |
| 7,179,484 B2 * | 2/2007 | Singh | 424/450 |
| 7,186,680 B2 * | 3/2007 | Caswell et al. | 512/4 |
| 7,192,588 B2 * | 3/2007 | Gallili et al. | 424/184.1 |
| 7,220,365 B2 * | 5/2007 | Qu et al. | 252/70 |

| Patent | Kind | Date | Inventors | Class |
|---|---|---|---|---|
| 7,223,447 | B2* | 5/2007 | Brown et al. | 427/543 |
| 7,229,645 | B2* | 6/2007 | Maa et al. | 424/489 |
| 7,247,288 | B2* | 7/2007 | Kumta et al. | 423/308 |
| 7,278,843 | B2* | 10/2007 | Feldstein et al. | 425/6 |
| 7,288,616 | B2* | 10/2007 | Tamareselvy et al. | 526/333 |
| 7,326,691 | B2* | 2/2008 | Duddu et al. | 514/31 |
| 7,342,079 | B2* | 3/2008 | Sher et al. | 526/206 |
| 7,351,779 | B2* | 4/2008 | Iaccino et al. | 526/206 |
| 7,354,597 | B2* | 4/2008 | Johnson et al. | 424/426 |
| 7,363,726 | B2* | 4/2008 | Wang et al. | 34/286 |
| 7,369,797 | B2* | 5/2008 | Yoshida et al. | 399/256 |
| 7,374,779 | B2* | 5/2008 | Chen et al. | 424/451 |
| 7,423,103 | B2* | 9/2008 | Stavens et al. | 526/206 |
| 7,446,084 | B2* | 11/2008 | Barthel et al. | 510/296 |
| 7,448,379 | B2* | 11/2008 | Yamashita et al. | 128/203.15 |
| 7,465,468 | B1* | 12/2008 | Cheney et al. | 426/101 |
| 7,494,965 | B2* | 2/2009 | Caswell et al. | 510/406 |
| 7,497,877 | B2* | 3/2009 | Goedhart et al. | 8/137 |
| 7,513,121 | B2* | 4/2009 | Zurecki et al. | 62/64 |
| 7,513,132 | B2* | 4/2009 | Wright et al. | 68/18 F |
| 7,517,628 | B2* | 4/2009 | Hirano et al. | 430/110.2 |
| 7,534,304 | B2* | 5/2009 | Conrad et al. | 134/10 |
| 7,534,758 | B2* | 5/2009 | Caswell et al. | 510/418 |
| 7,544,651 | B2* | 6/2009 | Caswell et al. | 510/439 |
| 7,553,440 | B2* | 6/2009 | Leonard | 264/413 |
| 7,578,960 | B2* | 8/2009 | Forbes Jones et al. | 266/202 |
| 7,624,595 | B2* | 12/2009 | Jeanvoine et al. | 65/157 |
| 7,628,999 | B2* | 12/2009 | Sunkara | 424/401 |
| 7,629,331 | B2* | 12/2009 | Pipkin et al. | 514/54 |
| 7,642,533 | B2* | 1/2010 | Partio et al. | 250/504 R |
| 7,645,351 | B2* | 1/2010 | Ohno et al. | 149/2 |
| 7,649,047 | B2* | 1/2010 | Tamareselvy et al. | 524/556 |
| 7,658,998 | B2* | 2/2010 | Brown et al. | 428/403 |
| 7,682,766 | B2* | 3/2010 | Fujimoto et al. | 430/123.42 |
| 7,731,954 | B2* | 6/2010 | Davis et al. | 424/94.4 |
| 7,735,485 | B2* | 6/2010 | Yamashita et al. | 128/202.17 |
| 7,758,327 | B2* | 7/2010 | Leonard | 425/93 |
| 7,767,249 | B2* | 8/2010 | Chinea et al. | 427/2.1 |
| 7,836,606 | B2* | 11/2010 | Gehrmann et al. | 34/284 |
| 2001/0024716 | A1* | 9/2001 | Chen et al. | 428/317.9 |
| 2001/0041743 | A1* | 11/2001 | Offenbacher et al. | 514/573 |
| 2002/0018837 | A1* | 2/2002 | Lanner et al. | 426/560 |
| 2002/0018838 | A1* | 2/2002 | Zimmerman et al. | 426/560 |
| 2002/0022076 | A1* | 2/2002 | Lanner et al. | 426/560 |
| 2002/0028273 | A1* | 3/2002 | Teras et al. | 426/439 |
| 2002/0034571 | A1* | 3/2002 | Zimmerman et al. | 426/549 |
| 2002/0050072 | A1* | 5/2002 | Akimoto et al. | 34/92 |
| 2002/0061336 | A1* | 5/2002 | O'Connor et al. | 424/499 |
| 2002/0063235 | A1* | 5/2002 | Fahy et al. | 252/70 |
| 2002/0072509 | A1* | 6/2002 | Stein et al. | 514/169 |
| 2002/0090345 | A1* | 7/2002 | Baichwal et al. | 424/46 |
| 2002/0094533 | A1* | 7/2002 | Hess et al. | 435/6 |
| 2002/0117170 | A1* | 8/2002 | Platz et al. | 128/200.14 |
| 2002/0120228 | A1* | 8/2002 | Maa et al. | 604/57 |
| 2002/0127188 | A1* | 9/2002 | Platz et al. | 424/46 |
| 2002/0146394 | A1* | 10/2002 | Stamets | 424/93.5 |
| 2002/0151604 | A1* | 10/2002 | Detering et al. | 518/703 |
| 2002/0187182 | A1* | 12/2002 | Kramer et al. | 424/443 |
| 2002/0189127 | A1* | 12/2002 | Akimoto et al. | 34/92 |
| 2002/0193290 | A1* | 12/2002 | Feldstein et al. | 514/2 |
| 2003/0006326 | A1* | 1/2003 | Inoki et al. | 241/65 |
| 2003/0026813 | A1* | 2/2003 | Gallili et al. | 424/204.1 |
| 2003/0029197 | A1* | 2/2003 | Jeanvoine et al. | 65/157 |
| 2003/0040462 | A1* | 2/2003 | Franks et al. | 514/1 |
| 2003/0059435 | A1* | 3/2003 | Gallili et al. | 424/184.1 |
| 2003/0064097 | A1* | 4/2003 | Patel et al. | 424/465 |
| 2003/0066638 | A1* | 4/2003 | Qu et al. | 165/186 |
| 2003/0068279 | A1* | 4/2003 | Platz et al. | 424/46 |
| 2003/0077297 | A1* | 4/2003 | Chen et al. | 424/400 |
| 2003/0086877 | A1* | 5/2003 | Platz et al. | 424/46 |
| 2003/0096899 | A1* | 5/2003 | Pearce | 524/474 |
| 2003/0098438 | A1* | 5/2003 | Haslin | 252/70 |
| 2003/0101995 | A1* | 6/2003 | Yamashita et al. | 128/203.15 |
| 2003/0104969 | A1* | 6/2003 | Caswell et al. | 510/513 |
| 2003/0116748 | A1* | 6/2003 | Haslim | 252/70 |
| 2003/0124716 | A1* | 7/2003 | Hess et al. | 435/287.1 |
| 2003/0129141 | A1* | 7/2003 | Platz et al. | 424/46 |
| 2003/0133876 | A1* | 7/2003 | Sutton et al. | 424/9.5 |
| 2003/0180352 | A1* | 9/2003 | Patel et al. | 424/465 |
| 2003/0180755 | A1 | 9/2003 | Hwang et al. | |
| 2003/0180807 | A1* | 9/2003 | Hess et al. | 435/7.1 |
| 2003/0185765 | A1* | 10/2003 | Platz et al. | 424/46 |
| 2003/0186271 | A1 | 10/2003 | Hwang et al. | |
| 2003/0194506 | A1* | 10/2003 | Drzal et al. | 427/553 |
| 2003/0198601 | A1* | 10/2003 | Platz et al. | 424/46 |
| 2003/0202978 | A1* | 10/2003 | Maa et al. | 424/184.1 |
| 2003/0207988 | A1* | 11/2003 | Tamareselvy et al. | 524/800 |
| 2003/0215496 | A1* | 11/2003 | Patel et al. | 424/452 |
| 2003/0219466 | A1* | 11/2003 | Kumta et al. | 424/423 |
| 2003/0220039 | A1* | 11/2003 | Chen et al. | 442/327 |
| 2003/0232020 | A1* | 12/2003 | York et al. | 424/46 |
| 2003/0232892 | A1* | 12/2003 | Guerra-Santos et al. | 514/684 |
| 2004/0036054 | A1* | 2/2004 | Haslim | 252/70 |
| 2004/0043042 | A1* | 3/2004 | Johnson et al. | 424/400 |
| 2004/0099612 | A1* | 5/2004 | Herbert et al. | 210/770 |
| 2004/0117919 | A1* | 6/2004 | Conrad et al. | 8/137 |
| 2004/0139555 | A1* | 7/2004 | Conrad et al. | 8/137 |
| 2004/0154317 | A1* | 8/2004 | Shekunov et al. | 62/64 |
| 2004/0162333 | A1* | 8/2004 | Mezaache et al. | 514/419 |
| 2004/0173146 | A1* | 9/2004 | Figueroa et al. | 118/325 |
| 2004/0173147 | A1* | 9/2004 | Figueroa et al. | 118/325 |
| 2004/0175331 | A1* | 9/2004 | Figueroa et al. | 424/45 |
| 2004/0206124 | A1* | 10/2004 | Jeanvoine et al. | 65/134.2 |
| 2004/0226098 | A1* | 11/2004 | Pearce | 5/655.5 |
| 2004/0226099 | A1* | 11/2004 | Pearce | 5/655.5 |
| 2004/0226726 | A1* | 11/2004 | Holland et al. | 169/62 |
| 2004/0229986 | A1* | 11/2004 | Pearce | 524/380 |
| 2004/0241800 | A1* | 12/2004 | Jue et al. | 435/69.1 |
| 2004/0247660 | A1* | 12/2004 | Singh | 424/450 |
| 2004/0247870 | A1* | 12/2004 | Brown et al. | 428/402 |
| 2005/0017396 | A1* | 1/2005 | Pearce et al. | 264/148 |
| 2005/0026793 | A1* | 2/2005 | Caswell et al. | 510/101 |
| 2005/0089548 | A1* | 4/2005 | Virgalitto et al. | 424/440 |
| 2005/0089576 | A1* | 4/2005 | Moreau | 424/486 |
| 2005/0091755 | A1* | 5/2005 | Conrad et al. | 8/137 |
| 2005/0091756 | A1* | 5/2005 | Wright et al. | 8/137 |
| 2005/0092352 | A1* | 5/2005 | Luckman et al. | 134/42 |
| 2005/0106553 | A1* | 5/2005 | Franks et al. | 435/2 |
| 2005/0118939 | A1* | 6/2005 | Duescher | 451/527 |
| 2005/0119165 | A1* | 6/2005 | Jue et al. | 514/8 |
| 2005/0126606 | A1* | 6/2005 | Goedhart et al. | 134/42 |
| 2005/0150059 | A1* | 7/2005 | Luckman et al. | 8/137 |
| 2005/0152946 | A1* | 7/2005 | Hunter et al. | 424/423 |
| 2005/0154374 | A1* | 7/2005 | Hunter et al. | 604/890.1 |
| 2005/0155393 | A1* | 7/2005 | Wright et al. | 68/3 R |
| 2005/0158356 | A1* | 7/2005 | Hunter et al. | 424/423 |
| 2005/0160615 | A1* | 7/2005 | Wang et al. | 34/92 |
| 2005/0161845 | A1* | 7/2005 | Haas | 264/5 |
| 2005/0169960 | A1* | 8/2005 | Hunter et al. | 424/423 |
| 2005/0169961 | A1* | 8/2005 | Hunter et al. | 424/423 |
| 2005/0175664 | A1* | 8/2005 | Hunter et al. | 424/423 |
| 2005/0175665 | A1* | 8/2005 | Hunter et al. | 424/423 |
| 2005/0175703 | A1* | 8/2005 | Hunter et al. | 424/486 |
| 2005/0176611 | A1* | 8/2005 | Caswell et al. | 510/295 |
| 2005/0178020 | A1* | 8/2005 | Shekunov et al. | 34/284 |
| 2005/0178395 | A1* | 8/2005 | Hunter et al. | 128/898 |
| 2005/0178396 | A1* | 8/2005 | Hunter et al. | 128/898 |
| 2005/0181005 | A1* | 8/2005 | Hunter et al. | 424/422 |
| 2005/0181009 | A1* | 8/2005 | Hunter et al. | 424/423 |
| 2005/0181010 | A1* | 8/2005 | Hunter et al. | 424/423 |
| 2005/0182463 | A1* | 8/2005 | Hunter et al. | 607/115 |
| 2005/0183731 | A1* | 8/2005 | Hunter et al. | 128/898 |
| 2005/0186239 | A1* | 8/2005 | Hunter et al. | 424/422 |
| 2005/0186244 | A1* | 8/2005 | Hunter et al. | 424/423 |
| 2005/0186245 | A1* | 8/2005 | Hunter et al. | 424/423 |
| 2005/0187140 | A1* | 8/2005 | Hunter et al. | 514/2 |
| 2005/0187188 | A1* | 8/2005 | Stein et al. | 514/58 |
| 2005/0189049 | A1* | 9/2005 | Ohno et al. | 149/2 |
| 2005/0191361 | A1* | 9/2005 | O'Connor et al. | 424/489 |
| 2005/0196421 | A1* | 9/2005 | Hunter et al. | 424/423 |
| 2005/0202990 | A1* | 9/2005 | Caswell et al. | 510/295 |
| 2005/0208095 | A1* | 9/2005 | Hunter et al. | 424/423 |
| 2005/0211029 | A1* | 9/2005 | Zurecki et al. | 82/1.11 |
| 2005/0214227 | A1* | 9/2005 | Prestrelski et al. | 424/46 |

| Publication | Date | Inventor | Ref |
|---|---|---|---|
| 2005/0238586 A1* | 10/2005 | Sutton et al. | 424/9.52 |
| 2005/0260273 A1* | 11/2005 | Chinea et al. | 424/489 |
| 2005/0260274 A1* | 11/2005 | Chinea et al. | 424/489 |
| 2005/0266021 A1* | 12/2005 | Maa et al. | 424/204.1 |
| 2005/0271737 A1* | 12/2005 | Chinea et al. | 424/490 |
| 2006/0025355 A1* | 2/2006 | Duddu et al. | 514/28 |
| 2006/0034816 A1* | 2/2006 | Davis et al. | 424/94.4 |
| 2006/0034903 A1* | 2/2006 | Maa et al. | 424/448 |
| 2006/0034937 A1* | 2/2006 | Patel | 424/497 |
| 2006/0035027 A1* | 2/2006 | Brown et al. | 427/320 |
| 2006/0053791 A1* | 3/2006 | Prentice | 60/645 |
| 2006/0057106 A1* | 3/2006 | Yamashita et al. | 424/85.6 |
| 2006/0057213 A1* | 3/2006 | Larhrib et al. | 424/489 |
| 2006/0073105 A1* | 4/2006 | Yamashita et al. | 424/46 |
| 2006/0123556 A1* | 6/2006 | Caswell et al. | 8/115.51 |
| 2006/0123557 A1* | 6/2006 | Caswell et al. | 8/115.51 |
| 2006/0130355 A1* | 6/2006 | Wang et al. | 34/284 |
| 2006/0135921 A1* | 6/2006 | Wiercinski et al. | 604/368 |
| 2006/0144869 A1* | 7/2006 | Chang et al. | 222/386 |
| 2006/0147389 A1* | 7/2006 | Staniforth et al. | 424/46 |
| 2006/0157507 A1* | 7/2006 | Chang et al. | 222/145.5 |
| 2006/0159821 A1* | 7/2006 | Brisson et al. | 426/565 |
| 2006/0191375 A1* | 8/2006 | Feldstein et al. | 75/338 |
| 2006/0204282 A1* | 9/2006 | Yoshida et al. | 399/254 |
| 2006/0210622 A1* | 9/2006 | Pace et al. | 424/456 |
| 2006/0225422 A1* | 10/2006 | Prentice | 60/645 |
| 2006/0253988 A1* | 11/2006 | Pearce | 5/655.5 |
| 2006/0254419 A1* | 11/2006 | Leonard | 95/57 |
| 2006/0269861 A1* | 11/2006 | Hirano et al. | 430/110.2 |
| 2006/0286205 A1* | 12/2006 | Fichtali et al. | 426/7 |
| 2007/0003492 A1* | 1/2007 | Kitahata et al. | 424/49 |
| 2007/0019148 A1* | 1/2007 | Ueda | 349/155 |
| 2007/0042048 A1* | 2/2007 | Platz et al. | 424/489 |
| 2007/0043030 A1* | 2/2007 | Morton et al. | 514/221 |
| 2007/0057416 A1* | 3/2007 | Kennedy | 266/202 |
| 2007/0062332 A1* | 3/2007 | Jones et al. | 75/338 |
| 2007/0065371 A2* | 3/2007 | Yamashita et al. | 424/46 |
| 2007/0093440 A1* | 4/2007 | Champion et al. | 514/44 |
| 2007/0111918 A1* | 5/2007 | Caswell et al. | 510/295 |
| 2007/0114298 A1* | 5/2007 | O'Keefe | 239/2.1 |
| 2007/0117939 A1* | 5/2007 | Iaccino et al. | 526/90 |
| 2007/0122418 A1* | 5/2007 | Platz et al. | 424/184.1 |
| 2007/0123477 A1* | 5/2007 | Malcolmson et al. | 514/28 |
| 2007/0129297 A1* | 6/2007 | Cochrane | 514/12 |
| 2007/0166368 A1* | 7/2007 | Singh | 424/450 |
| 2007/0167340 A1* | 7/2007 | Barthel et al. | 510/220 |
| 2007/0178399 A1* | 8/2007 | Kobayashi et al. | 430/124.3 |
| 2007/0190158 A1* | 8/2007 | Hwang et al. | 424/489 |
| 2007/0197957 A1* | 8/2007 | Hunter et al. | 604/65 |
| 2007/0202342 A1* | 8/2007 | Whiteford et al. | 428/425.5 |
| 2007/0203047 A1* | 8/2007 | Pegelow et al. | 510/421 |
| 2007/0203209 A1* | 8/2007 | Bartolini et al. | 514/367 |
| 2007/0208154 A1* | 9/2007 | Stavens et al. | 526/280 |
| 2007/0219325 A1* | 9/2007 | Sher et al. | 526/68 |
| 2007/0224128 A1* | 9/2007 | Dennis et al. | 424/10.1 |
| 2007/0241306 A1* | 10/2007 | Wehner et al. | 252/67 |
| 2007/0254233 A1* | 11/2007 | Fujimoto et al. | 430/123.42 |
| 2007/0269392 A1* | 11/2007 | Sunkara | 424/59 |
| 2008/0009432 A1* | 1/2008 | Caswell et al. | 510/439 |
| 2008/0020127 A1* | 1/2008 | Whiteford et al. | 427/2.1 |
| 2008/0021212 A1* | 1/2008 | Whiteford et al. | 540/472 |
| 2008/0023657 A1* | 1/2008 | Melnychuk et al. | 250/504 R |
| 2008/0026068 A1* | 1/2008 | Brown et al. | 424/489 |
| 2008/0038356 A1* | 2/2008 | Maa et al. | 424/489 |
| 2008/0045646 A1* | 2/2008 | Tamareselvy et al. | 524/555 |
| 2008/0050793 A1* | 2/2008 | Durance et al. | 435/173.1 |
| 2008/0060213 A1* | 3/2008 | Gehrmann et al. | 34/284 |
| 2008/0075777 A1* | 3/2008 | Kennedy | 424/484 |
| 2008/0091233 A1* | 4/2008 | Ellis-Behnke et al. | 606/213 |
| 2008/0095820 A1* | 4/2008 | Kumta et al. | 424/423 |
| 2008/0142166 A1* | 6/2008 | Carson et al. | 159/4.01 |
| 2008/0145658 A1* | 6/2008 | Richard et al. | 428/402 |
| 2008/0155853 A1* | 7/2008 | Wang et al. | 34/285 |
| 2008/0161233 A1* | 7/2008 | Moreau | 514/11 |
| 2008/0172047 A1* | 7/2008 | Altshuler et al. | 606/9 |
| 2008/0179034 A1* | 7/2008 | Forbes Jones et al. | 164/46 |
| 2008/0183162 A1* | 7/2008 | Altshuler et al. | 606/9 |
| 2008/0194494 A1* | 8/2008 | Martinez et al. | 514/25 |
| 2008/0207581 A1* | 8/2008 | Whiteford et al. | 514/183 |
| 2008/0214988 A1* | 9/2008 | Altshuler et al. | 604/21 |
| 2008/0223758 A1* | 9/2008 | Scheeres | 209/3 |
| 2008/0241269 A1* | 10/2008 | Velasquez | 424/520 |
| 2008/0305271 A1* | 12/2008 | Ring et al. | 427/459 |
| 2008/0306471 A1* | 12/2008 | Altshuler et al. | 606/10 |
| 2009/0000758 A1* | 1/2009 | Stone et al. | 164/316 |
| 2009/0011037 A1* | 1/2009 | Pipkin et al. | 424/499 |
| 2009/0016964 A1* | 1/2009 | Kalechofsky et al. | 424/9.3 |
| 2009/0053318 A1* | 2/2009 | Tan et al. | 424/501 |
| 2009/0059138 A1* | 3/2009 | Matsumoto et al. | 349/106 |
| 2009/0062173 A1* | 3/2009 | Caswell et al. | 510/295 |
| 2009/0069741 A1* | 3/2009 | Altshuler et al. | 604/22 |
| 2009/0074859 A1* | 3/2009 | Patel | 424/457 |
| 2009/0095293 A1* | 4/2009 | Yamashita et al. | 128/203.15 |
| 2009/0118503 A1* | 5/2009 | Sprott et al. | 544/143 |
| 2009/0123540 A1* | 5/2009 | Pipkin et al. | 424/468 |
| 2009/0126732 A1* | 5/2009 | Yamashita et al. | 128/203.15 |
| 2009/0131395 A1* | 5/2009 | Antonelli et al. | 514/210.02 |
| 2009/0136737 A1* | 5/2009 | Ring et al. | 428/323 |
| 2009/0169500 A1* | 7/2009 | Sunkara | 424/65 |
| 2009/0190073 A1* | 7/2009 | Yoshino et al. | 349/106 |
| 2009/0238878 A1* | 9/2009 | Singh | 424/489 |
| 2009/0263555 A1* | 10/2009 | Tapfer et al. | 426/564 |
| 2009/0264653 A1* | 10/2009 | Bartolini et al. | 544/238 |
| 2009/0272228 A1* | 11/2009 | Forbes Jones et al. | 75/331 |
| 2009/0272269 A1* | 11/2009 | Leonard | 95/285 |
| 2009/0280534 A1* | 11/2009 | Christensen et al. | 435/69.6 |
| 2009/0311406 A1* | 12/2009 | Tapfer et al. | 426/565 |
| 2009/0312724 A1* | 12/2009 | Pipkin et al. | 604/294 |
| 2009/0323459 A1* | 12/2009 | Windhab et al. | 366/105 |
| 2010/0035789 A1* | 2/2010 | Caswell et al. | 510/296 |
| 2010/0055049 A1* | 3/2010 | Kuo et al. | 424/46 |
| 2010/0055266 A1* | 3/2010 | Windhab et al. | 426/317 |
| 2010/0076108 A1* | 3/2010 | Miyashita et al. | 522/75 |
| 2010/0115708 A1* | 5/2010 | Caswell et al. | 8/137 |
| 2010/0168011 A1* | 7/2010 | Jennings et al. | 514/12 |
| 2010/0173005 A1* | 7/2010 | Prestrelski et al. | 424/497 |
| 2010/0190722 A1* | 7/2010 | Bevec et al. | 514/15 |
| 2010/0197708 A1* | 8/2010 | Talley et al. | 514/269 |
| 2010/0247712 A1* | 9/2010 | Rudolph | 426/61 |
| 2010/0258118 A1* | 10/2010 | Morton | 128/203.15 |
| 2010/0263696 A1* | 10/2010 | Leonard | 134/172 |
| 2010/0326437 A1* | 12/2010 | Zeng | 128/203.15 |
| 2011/0020947 A1* | 1/2011 | Bedingham et al. | 436/174 |

FOREIGN PATENT DOCUMENTS

| | | |
|---|---|---|
| CA | 2375250 | 12/2000 |
| CA | 2386206 | 4/2001 |
| DE | 4200678 A1 * | 7/1992 |
| DE | 4113512 | 10/1992 |
| DE | 19750679 A1 * | 5/1999 |
| EP | 546597 A1 * | 6/1993 |
| JP | S53-114783 | 10/1978 |
| JP | 55015788 A * | 2/1980 |
| JP | 55102369 A * | 8/1980 |
| JP | 58138347 A * | 8/1983 |
| JP | 60096530 A * | 5/1985 |
| JP | 63017670 A * | 1/1988 |
| JP | S63-36817 | 7/1988 |
| JP | 03004946 A * | 1/1991 |
| JP | 06062744 A * | 3/1994 |
| JP | 06292705 A * | 10/1994 |
| JP | H07-080271 | 3/1995 |
| JP | 08280807 A * | 10/1996 |
| JP | 11178509 A * | 7/1999 |
| JP | 2001-518391 | 10/2001 |
| JP | 2002-058981 | 2/2002 |
| JP | 2002338965 A * | 11/2002 |
| WO | 7900086 A1 | 2/1979 |
| WO | WO 8810150 A1 * | 12/1988 |
| WO | WO 03043574 A2 * | 5/2003 |
| WO | 03072016 | 9/2003 |
| WO | 2005021807 | 3/2005 |
| WO | WO 2005061088 A1 * | 7/2005 |

OTHER PUBLICATIONS

S. Wayne Klein, Sol H. Goodgal, "Sublimation Freeze-Drying without Vacuum", Science, 1959, 130: 628-629.

Takashina, J. Japanese Patent Application H07-080271 (English Machine Translation), 1995.

Kitamura et al., Japanese Patent Application JP2002058981 (English Machine Translation), 2002.

* cited by examiner

POWDER FORMATION BY ATMOSPHERIC SPRAY-FREEZE DRYING

This application is a continuation of U.S. patent application Ser. No. 11/318,864 filed Dec. 28, 2005 now U.S. Pat. No. 7,363,726. U.S. patent application Ser. No. 11/318,864 is a continuation of U.S. patent application Ser. No. 10/762,300 filed Jan. 23, 2004, now U.S. Pat. No. 7,007,406.

BACKGROUND OF THE INVENTION

This invention relates to the preparation of powders, particularly for the administration of pharmaceuticals to humans.

Pharmaceuticals are often unstable compounds that degrade rapidly during processes that lead to a powder form of the pharmaceutical. Since the pharmaceutical compound is usually carried in an aqueous solution, and the aqueous solution must be dried to form the powder, the required desiccation or drying process may easily damage the pharmaceutical. At the same time, if the process of forming the powder takes too long, or is too energy consuming, the process may become uneconomic.

Freeze drying (lyophilization), which has conventionally been used to prepare pharmaceutical powders, provides a two step preservation and dehydration process in which the product is first frozen and the water is then removed as vapor from the frozen state. As the water passes from the solid phase directly into the vapor phase, it is necessary that the vapor pressure and the temperature of the sublimation zone is held below those of the triple point on the phase diagram for water. The temperature ($<<0°$ C.) and the maintenance of the frozen state lead to very low driving forces for heat and mass transfer and therefore, often to very low drying rates and very long drying times. Thus, despite its capability of providing a very high-quality dehydrated product, freeze-drying has been and remains highly energy-intensive and consequently, is a very expensive dehydration process.

Freeze drying conventionally is carried out in a vacuum, but may also be carried out at or near atmospheric pressure. Atmospheric freeze-drying has been shown to have the added advantage of increasing transfer coefficients and improving the uniformity of the product during lyophilization. For example, Meryman, H. T., Sublimation freeze-drying without vacuum. *Science,* 130 (1959) 628-629 proposed an atmospheric freeze-drying process in which the partial pressure of water in the drying chamber is held at very low value and he suggested that such a process should be based on the principle of convective freeze drying, i.e. a cold air steam, kept dry by a molecular sieve desiccant or by a refrigerated condenser, should be circulated. More recently, Leuenberger, H., Spray freeze-drying—the process of choice for low water soluble drugs, *Journal of Nanoparticle Research,* 4:111-119, 2002 has also identified that spray freeze drying helps preserve pharmacological activity of drugs by stabilization in an appropriate matrix.

Despite the potential advantages of atmospheric lyophilization, the challenge still remains to provide a combination of spray-freezing solution/suspension into liquid and atmospheric freeze-drying that meets industrial demands for a pharmaceutical powder process that maintains drug bioactivity at low economic cost.

SUMMARY OF THE INVENTION

It is therefore an object of this invention to provide atmospheric spray freeze drying of liquid carrying pharmaceuticals to produce a powder by a pharmaceutical powder process that maintains drug bioactivity at low economic cost. The invention provides a method of manufacturing a powder or particulate pharmaceutical substance, and an apparatus for carrying out the method. The powder produced by this process is believed to exhibit higher emitted dose and better preservation of bioactivity than spray-dried particles and milled particles. In addition, the porous nature of the particles provides rapid dissolution properties. The invention is applicable to the formation of other powders, including powder forms of nutraceuticals and foods.

Therefore, according to an aspect of the invention, there is provided a method of creating a powder, comprising spraying a carrier liquid containing a powder forming ingredient to form a flow of liquid droplets; entraining the flow with a coolant for sufficient time to freeze the liquid droplets into frozen particles; and drying the frozen particles to form a dry powder.

According to a further aspect of the invention, there is provided apparatus for atmospheric spray freeze drying of an ingredient carrying liquid to form a powder, the apparatus comprising: a chamber having an atomizer at one end of the chamber, the atomizer being connected to a source of the ingredient carrier liquid to produce a flow of liquid droplets; a nozzle system for providing a flow of coolant that entrains atomized fluid sprayed by the atomizer; a source of coolant for the nozzle system; and a collector spaced from the atomizer sufficiently that liquid droplets atomized by the atomizer are frozen by the flow of coolant before contact with the collector.

The powder forming ingredient may be suspended or dissolved in the carrier liquid. The entraining flow may be a concurrent flow of coolant, for example as sprayed from a ring nozzle or through porous side walls of a confining chamber. Frozen particles are preferably collected on a filter at an exit from the confining chamber, and drying mostly takes place on the filter. For enhanced drying, the flow over the filter should be at a warmer temperature than for freezing. More than one powder forming ingredient may be present in the carrier liquid.

Other aspects of the invention appear in the claims.

BRIEF DESCRIPTION OF THE DRAWINGS

There will now be described preferred embodiments of the invention with reference to the figures, by way of example, and without intending to limit the scope of the invention to the precise examples disclosed here, and in which figures.

DETAILED DESCRIPTION OF PREFERRED EMBODIMENTS OF THE INVENTION

The word "comprising" in the claims is used in its inclusive sense and does not exclude other elements being present. The use of the indefinite article "a" in a claim before an element does not exclude more than one of the element being present.

The present invention is widely applicable for producing particulate material and can be used for spray-freeze drying any material amenable to dissolution or suspension in a suitable carrier liquid, such as water. The term powder forming ingredient is used to refer to one or more pharmaceutical, nutraceutical, food or other substances that have utility in powder form. The present invention is especially useful for heat-sensitive substances, such as proteins, nucleic acids, oligonucleotides, enzymes, liposomes, lipids, lipid complexes, anti-virals and vaccines (e.g. involving nonvirulent or attenuated pathogens), carbohydrates, polymers, polysaccharides, and peptides. However, its use is not limited to only large molecules, since the method always produces a powder from any material dissolved or suitably suspended in water; it may be used to create, for example, powder anti-infectives, anti-microbials, anti-inflammatories, antineoplastics, analgesics, anaesthetics, cholinergics, adrenergics, anticonvulsants, anti-depressants, sedatives, tranquilizers and antiemetics, immunosuppressives and immunostimulants, antihistamines, hormones, antivenoms and antitoxins. Cryoprotectants may be added to aid in preventing degradation of substances during processing. The ingredient carrying liquid may contain several different drugs and also excipient material. For example, the particles may be made mostly out of lactose with only a little drug in them. Or there may be several drugs in the ingredient carrying liquid, plus lactose or other filler/matrix/excipient compound.

In the embodiments shown in FIGS. 1, 2 and 3, a flow or spray of atomized carrier fluid is frozen into a powder of solid particles by an entraining flow of coolant and subsequently dried by providing a flow of desiccating gas over the powder. Entraining by the cooling gas provides for confining the spray, and immediate freezing of the individual spray droplets, so that the liquid spray droplets do not impact on the walls of the chamber in which the process is carried out.

Figure 1:
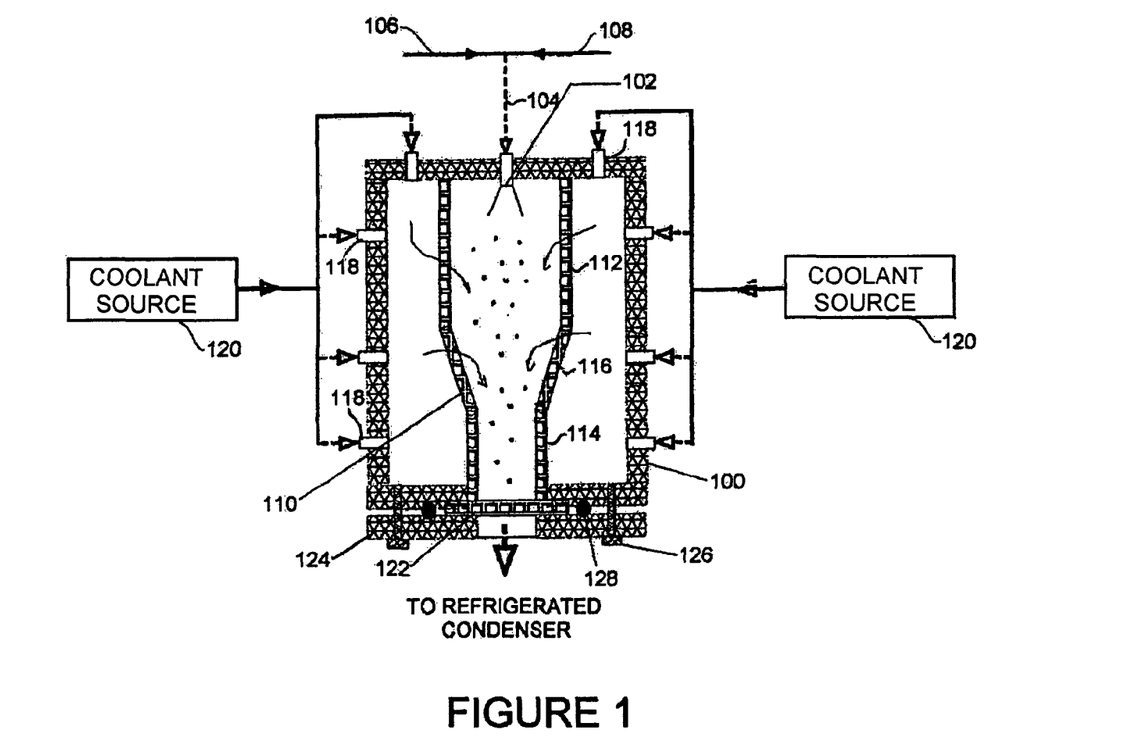
FIG. 1 shows a first embodiment of a device for accomplishing atmospheric spray freeze drying according to the invention.

Referring to the first embodiment shown in FIG. 1, a housing 100 formed with solid insulated walls supports at an inlet end an atomizer 102 that is supplied through line 104 with compressed gas from source 106 and a suitable carrier liquid from source 108. Inside the housing 100 is a flow chamber 110 with porous walls. The flow chamber 110 is formed of cylindrical sections 112, 114 of differing diameter joined by a conical section 116. Multiple nozzles 118 of a nozzle system penetrate the housing 100 and supply a cryogenic flow of coolant from a coolant source 120 into the space between the housing 100 and flow chamber 110. At the other, exit, end of the housing 100 from the atomizer 102, the flow chamber 110 terminates in a filter 122 that is held across an opening in the housing 100 by a plate 124 fixed to the chamber 100 by bolts or clamps 126 with O-ring 128. Gas flow from the exit end of the housing 100 is returned to a refrigerated condenser that forms part of the coolant source 120. The refrigerated condenser strips moisture from the cooling gas for re-use of the cooling gas.

Figure 2:
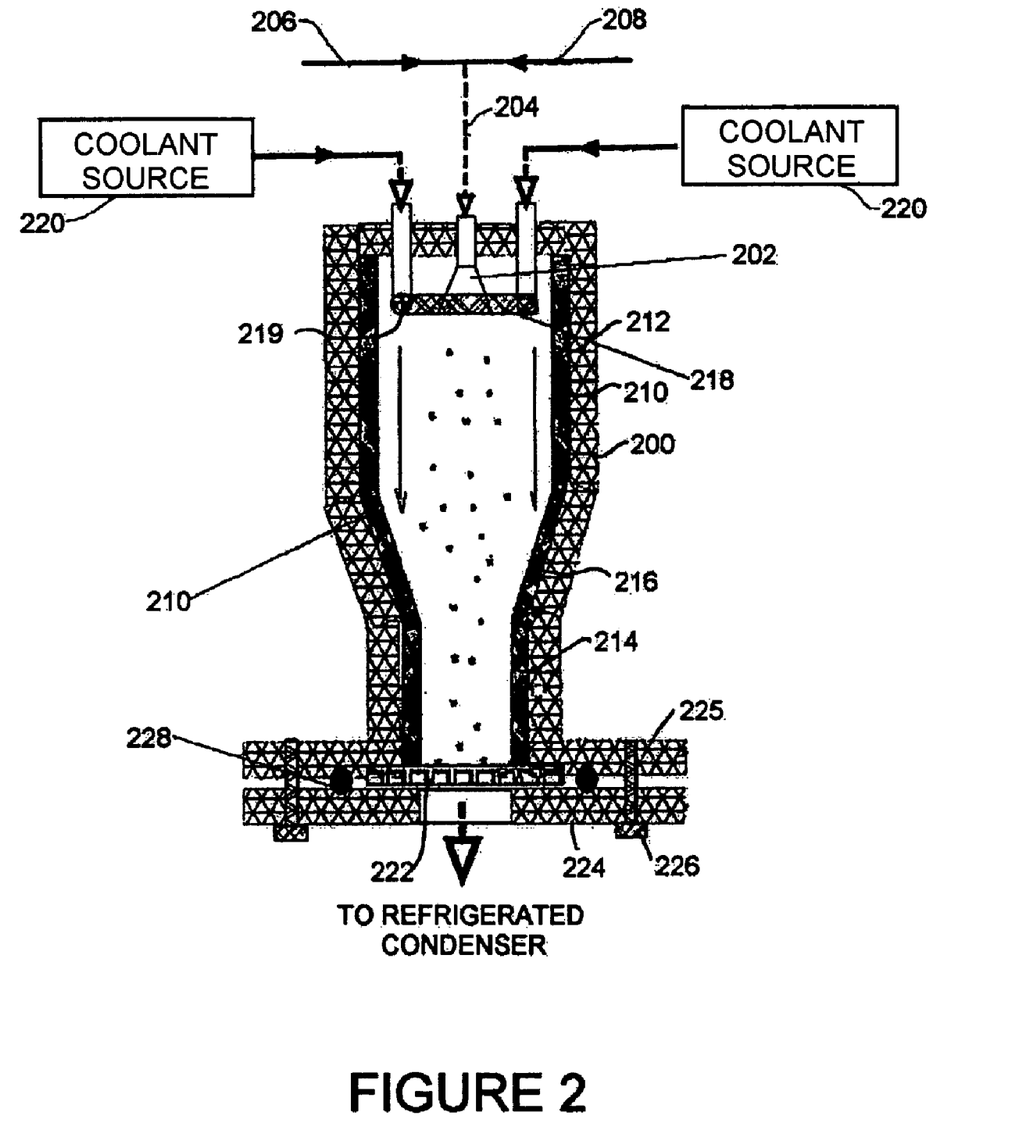
FIG. 2 shows a second embodiment of a device for accomplishing atmospheric spray freeze drying according to the invention.

Referring to a second embodiment shown in FIG. 2, a housing 200 formed with solid insulated walls supports at an inlet end an atomizer 202 that is supplied through line 204 with compressed gas from source 206 and a suitable carrier liquid from source 208. Inside the housing 200 is a flow chamber 210 defined by solid walls lining the housing 200. The flow chamber 210 is formed of cylindrical sections 212, 214 of differing diameter joined by a conical section 216. Surrounding the atomizer 202 is a nozzle system in the form of a ring nozzle 218, with openings 219 directing flow from the ring nozzle 218 parallel to flow from the atomizer 202. The ring nozzle 218 supplies a cryogenic flow of coolant from a coolant source 220, for example a liquid nitrogen cylinder driven by compressed gas that surrounds flow from the atomizer 202 in the spray-freezing step and a refrigerated condenser in the following drying step. At the other, exit, end of the housing 200 from the atomizer 202, the flow chamber 210 terminates in a filter 222 that is held across an opening in the housing 200 by a plate 224 fixed to flanges 225 on the chamber 200 by bolts or clamps 226 with O-ring 228.

Figure 3:
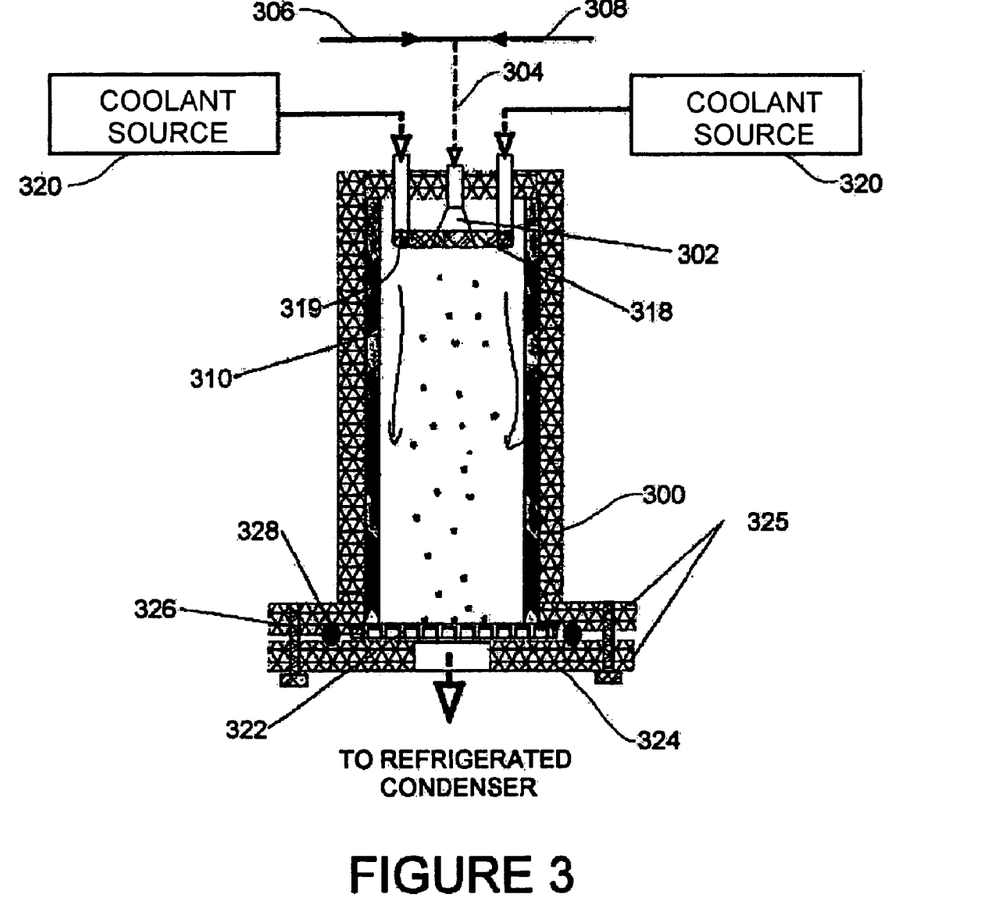
FIG. 3 shows a third embodiment of a device for accomplishing atmospheric spray freeze drying according to the invention.

Referring to a third embodiment shown in FIG. 3, a housing 300 formed with solid insulated walls supports at an inlet end an atomizer 302 that is supplied through line 304 with compressed gas from source 306 and a suitable carrier liquid from source 308. Inside the housing 300 is a cylindrical flow chamber 310 defined by solid walls lining the housing 300. Surrounding the atomizer 302 is a ring nozzle 318, with openings 319 directing flow from the ring nozzle 318 parallel to flow from the atomizer 302. The ring nozzle 318 supplies a cryogenic flow of coolant from a coolant source 320, for example a liquid nitrogen cylinder driven by compressed gas that surrounds flow from the atomizer 302 in the spray-freezing step and a refrigerated condenser in the following drying step. At the other, exit, end of the housing 300 from the atomizer 302, the flow chamber 310 terminates in a filter 322 that is held across an opening in the housing 300 by a plate 324 fixed to flanges 325 on the chamber 300 by bolts or clamps 326 with O-ring 328.

The coolant source 120, 220 or 320 may be any source of a coolant that does not contaminate or degrade the powder. Cold gas may be used such as refrigerated nitrogen, particularly for the embodiment shown in FIG. 1. The nitrogen may also be obtained from a liquid nitrogen cylinder driven by compressed gas, particularly for the embodiment shown in FIGS. 2 and 3. Upon exiting the nozzles 118, 218 and 318, cold gas or liquid, for example cold liquid nitrogen or cold gaseous nitrogen, which may be sourced from a cylinder of liquid nitrogen or other cryogenic source of nitrogen, will entrain the spray and freeze the liquid drops of the spray. For freezing followed by drying, both a liquid nitrogen source and a refrigeration unit may be used. Freezing may be carried out using the liquid nitrogen source, as in the embodiment of FIGS. 2 and 3, and then drying may be carried out at warmer temperatures using the refrigeration unit.

During manufacture, pharmaceutical agents (PA) or other powder forming ingredients are mixed with a carrier liquid prior to spraying from the atomizer 102, 202, 302. The spray fluid resulting from the mixture of PA and carrier liquid may be, for example, a solution, a suspension or a colloid. The atomizer 102, 202, 302 may be a two-fluid nozzle or an ultrasonic nebulizer or a vibrating orifice aerosol generator (VOAG) or other atomizing device. The spray fluid, which is formed of liquid droplets, is rapidly frozen through contact with coolant, which is a cold fluid of a suitable temperature. In the spray-freeze step, cooling fluid may be supplied in several possible ways. One way, shown in FIGS. 2, 3, is to spray cooling liquid such as liquid nitrogen directly into the chamber 200,300 by using the ring nozzle 218, 318, while spray droplets from atomizer 202, 302 inside the perimeter of the ring nozzle 218, 318 are frozen immediately after contacting the surrounding curtain of liquid nitrogen and then conveyed to the exit filter 222, 322 at the exit end of the housing 200, 300. Another way, shown in FIG. 1, is to have a cooling gas enter through porous walls 112, 114, 116 that enclose the atomizer 102. Gas supplied into the space between the housing 100 and chamber 110 forms a gas jacket whose temperature is adjusted by mixing with liquid nitrogen or an equivalent cryogenic at different ratios.

In the example of FIGS. 2 and 3, the curtain of spraying liquid nitrogen is used for freezing the spraying liquid droplets and avoiding cohesion of frozen powder on the sidewalls 210, 310. The spraying velocity and quantity of liquid nitrogen is controlled to meet both the cooling demand of the spray-freeze process and conveying of frozen powders to the exit filter 222, 322. In the example of FIG. 1, the flow passing through the porous sidewalls of the freezing chamber 110 has the same function as the spraying curtain of liquid nitrogen, i.e. reducing the particle cohesion and allowing a distinguishingly radial flow of cooling fluid into the chamber 110 to freeze liquid droplets and protect the liquid droplet/frozen particles from contacting the wall surface. The thickness of the porous sidewall 110 and pressure inside the gas jacket, which is controlled by the flow rate of cooling gas into the chamber 100, are adjusted for the particular powder being processed. Thereafter, a down-flow transport by virtue of the spray direction of the atomizer 102 is automatically formed in the spray-freeze process to carry all the frozen powder to the exit end of the chamber 100.

After the accomplishment of spray-freezing, a proper drying temperature will be chosen in a drying step by flow rate adjustment from the cooling cryogenic or refrigeration system. In the meantime, the initial frozen powder collected on the exit filter 122, 222, 322 at exit end (bottom) of the chamber will be dried by sublimation in a cold desiccated airstream at atmospheric pressure. Because all the frozen powder falls down or is conveyed by the down stream flow to the exit filter, no matter whether it is cohesive powder or free flow powder, no external forces are needed to re-lift the powder adhering on the walls, unlike in the spray-freeze drying process of a traditional up-stream fluidized bed, which are used in other processes like U.S. Pat. No. 4,608,764.

In addition, less contamination is realized through this invention by screening frozen powder from contacting the sidewalls of the chamber 110, 210, 310 compared to the former technology. As the sublimation process is taking place, the frozen particles become lighter and the aerodynamic behavior changes. The partially dried particles may form a loose cake on the exit filter 122, 222, 322, from which the remaining moisture is removed by atmospheric sublimation using a cold desiccated gas stream, resulting in final free-flowing powders. After spray-freeze atmospheric drying, dry porous particles of roughly the same size and shape as the original frozen droplets are obtained.

Spray freeze atmospheric dried particles produced by this method can have a morphology desirable for respiratory administration of medicament using respiratory delivery devices such as those disclosed in U.S. patent application US60430085 filed Nov. 27, 2003. The typically porous nature of particles formed from this process is also desirable for rapid dissolution, as seen in the BioAqueous technology from Dow Chemical Company, as well as for other purposes such as those disclosed in e.g. U.S. Pat. No. 6,635,283.

Operating Procedures

The apparatus is allowed to run for approximately 5 to 30 minutes to reach the desired temperature in the chamber 110, 210, 310 either by spraying liquid nitrogen directly into it, or by having the cold fluid from a refrigeration system flow into the chamber 110 through the porous wall. The aqueous solution or suspension of the substances to be dried is then sprayed using the atomizer 102, 202, 302 and frozen simultaneously in situ at a chosen temperature by the surrounding curtain of liquid nitrogen generated from ring nozzle 218, 318 or an equivalent such as cryogenic flow from nozzles 118 through porous sidewalls of chamber 110. The frozen powder is conveyed down to the exit filter 122, 222, 322 by the concurrent downstream flow. After completion of the spray-freezing process, the flow of the cryogenic fluid (at a low temperature of −50° C. to −196° C.) is shut off and switched to a cooling gas at a somewhat higher temperature (−10° C. to −30° C.) from the refrigeration system. Then the frozen powder collected on the exit filter 122, 222, 322, at the bottom is dried continuously by sublimation at atmospheric pressure until the remaining moisture of the frozen powder is removed by the cold desiccated gas stream. After spray-freeze atmospheric drying, a loose cake occurs on the exit filter 122, 222, 322, which is very fragile and easily broken into free flowing, dry porous particles of approximately the same size and shape as the original frozen droplets. In order to reduce moisture condensation on the cold particle surface, the temperature of the desiccant cooling gas will be raised to room temperature gradually before the sample is collected from the chamber 100, 200, 300.

In one example, powder was produced using the method described above. A 15 wt % mannitol solution was spray freeze-dried using the apparatus shown in FIG. 1. A 15% mannitol (Mannitol USP powder, Fisher Scientific) aqueous solution was used to demonstrate the process. Before spraying, the chamber 110 for spray-freeze drying was allowed to run for approximately 20 minutes to reach the desired temperature (−65° C.). During the 20 minutes, the cold fluid from a refrigeration unit incorporating two parallel dry-ice cooling columns flows into the chamber 110 through the porous sidewall. A Chem-Tech pump (Model CTPA4LSA-PAP1-XXXX, Viking pump of Canada Inc, Windsor, Ontario, Canada) was used to pump 20 ml of 15% mannitol solution into an air atomizing spray nozzle 102 (Spraying Systems Co., Wheaton, Ill., USA) spraying into the chamber from the top with the aid of a compressed driving gas (nitrogen) at a flowrate of 0.6 SCFM. The spray-freezing process was finished within 4 minutes and meanwhile, the temperature in the chamber 110 was kept at −50° C. to −70° C. by the mixed cooling gas (nitrogen). In this case, the pressure in the chamber was almost atmospheric (around 1.02 atm). After the completion of spray-freeze process, the pump and driving gas for spraying was shut down and the cooling gas for drying was kept flowing at a flowrate of 60 L/min. The temperature in the chamber was kept at around −15° C. (−5° C. to −20° C.) by adjusting the height of dry ice in the cooling columns. After drying for 1 hr, the temperature in the chamber was raised to room temperature gradually within another 30 minutes at a flowrate of 30 L/min. Thereafter, the cooling gas was shut off and a dry powder cake on the exit filter 122 was collected. This cake was easily broken into a free-flowing powder and the resulting particles were found very porous and roughly spherical. The moisture content was measured to be only 0.9%. Photos from a scanning electron microscope (SEM) of one resulting sample powder collected from the exit filter showed that the powder particles are relatively spherical and considerably porous, which is often seen in spray-freeze drying with vacuum.

Mannitol has been spray-frozen by us at −50° C. to −70° C. and dried in a temperature of −5° C. to −20° C. in order to avoid mannitol crystallization (mannitol hydrate occurs at around 38° C.). Based on practical demand (each bio-substance may have its ideal spray-freeze and drying temperature), the spray-freeze drying conditions are adjustable by changing the temperature and flow rate of the mixed cold gases. Depending on the batch scale, these parameters may be different.

For atmospheric pressure freeze drying with dry air, the temperature at which material may be truly freeze dried is set by its melting point. Since the vapor pressure of ice is essentially fixed by the melting point temperature, the rate of freeze-drying is essentially controlled by the resistance to water vapor diffusion in the material. This resistance is proportional to the diffusion path length and the permeability of the material. Atmospheric pressure freeze-drying should therefore be feasible in a wide variety of materials where diffusion distances are very short in materials of open structure.

Immaterial modifications may be made to the invention described here without departing from the invention.

We claim:

1. A method of creating a powder, comprising the steps of:
spraying a carrier liquid into a chamber, the carrier liquid containing a powder forming ingredient to form a flow of liquid droplets containing the carrier liquid and powder forming ingredient;
entraining the flow of liquid droplets within a flow of coolant for sufficient time to freeze the liquid droplets into frozen particles, the flow of coolant entering the chamber around the flow of liquid droplets and frozen particles to screen the frozen particles from contacting walls of the chamber; and
drying the frozen particles to form a dry powder.

2. The method of claim 1 in which the powder forming ingredient is suspended or dissolved in the carrier liquid prior to spraying the carrier liquid into the chamber.

3. The method of claim 1 in which the flow of coolant is sprayed from a ring nozzle.

4. The method of claim 1 in which the flow of-coolant is injected through porous walls of the chamber.

5. The method of claim 1 in which the frozen particles are collected on a filter.

6. The method of claim 5 in which the frozen particles are substantially dried after being collected on the filter.

7. The method of claim 1 in which the flow of coolant has a temperature within a first temperature range during freezing of the liquid particles and a temperature warmer than the first temperature range during drying of the frozen particles.

8. The method of claim 1 in which the carrier liquid contains more than one powder forming ingredient.

9. The method of claim 1 in which the flow of coolant is co-current with the flow of liquid droplets.

10. The method of claim 1 in which spraying, entraining and freezing of the liquid droplets is carried out within the chamber.

11. The method of claim 10 in which deposition and drying of the frozen particles is carried out within the chamber.

12. The method of claim 1 further comprising depositing the frozen particles on a collector, the liquid droplets being frozen before deposition on the collector, and drying the frozen particles while the frozen particles are collected on the collector.

13. The method of claim 12 in which the collector is a filter at an exit to the chamber.

14. The method of claim 1 in which drying is carried out with a downward flow of coolant.

15. The method of claim 11 in which drying is carried out with a downward flow of coolant.

* * * * *